US012571787B2

(12) United States Patent
McFarlane, Jr.

(10) Patent No.: US 12,571,787 B2
(45) Date of Patent: Mar. 10, 2026

(54) ELECTROCHEMICAL SENSOR FOR SENSING TWO-PHASE COOLING FLUID CONTAMINATION

(71) Applicant: Microsoft Technology Licensing, LLC, Redmond, WA (US)

(72) Inventor: Robert Craig McFarlane, Jr., Sammamish, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 896 days.

(21) Appl. No.: 17/837,366

(22) Filed: Jun. 10, 2022

(65) Prior Publication Data

US 2023/0400444 A1    Dec. 14, 2023

(51) Int. Cl.
*G01N 33/18*      (2006.01)
*H05K 7/20*      (2006.01)

(52) U.S. Cl.
CPC ............. *G01N 33/18* (2013.01); *H05K 7/203* (2013.01)

(58) Field of Classification Search
CPC ........ G01N 27/026; G01N 33/18; G06F 1/20; G06F 2200/201; G06N 3/04; H05K 7/203; H05K 7/20818
See application file for complete search history.

(56) References Cited

U.S. PATENT DOCUMENTS 5,275,704 A  *  1/1994  Yang ...................... G01N 17/02
                                                            205/794.5
10,773,192 B1     9/2020  Lau 2011/0027628 A1*  2/2011  Deane ...................... H01M 4/02
                                                            429/61
2015/0253267 A1*  9/2015  Quellet ............ G06Q 10/06313
                                                            324/76.39
2021/0219455 A1     7/2021  Lau
2021/0349008 A1*  11/2021  Kinlen ................. G01N 33/442

FOREIGN PATENT DOCUMENTS

| JP | H04116758 | A | | 4/1992 |
| JP | H04116758 | U | * | 10/1992 |
| WO | 2021252789 | A1 | | 12/2021 |
| WO | 2022058915 | A1 | | 3/2022 |

OTHER PUBLICATIONS

Yamaguchi (JPH04116758U) English translation (Year: 2025).*
"International Search Report and Written Opinion Issued in PCT Application No. PCT/US23/019040", Mailed Date: Jun. 21, 2023, 13 Pages.

* cited by examiner

*Primary Examiner* — Jennifer Wecker
*Assistant Examiner* — Jonathan Bortoli
(74) *Attorney, Agent, or Firm* — Ray Quinney & Nebeker P.C.; John O. Carpenter

(57)            ABSTRACT

An immersion cooling system includes an immersion tank defining an immersion chamber therein, an immersion working fluid, a first electrode, and a second electrode. The immersion working fluid is positioned at least partially in the immersion chamber. The first electrode is electrically coupled to an electrical power source, and the second electrode is positioned proximate to the first electrode and defines a sampling region therebetween. A sample portion of the immersion working fluid is positioned in the sampling region, and the second electrode is coupled to a microcontroller configured to measure at least a current across the sampling region between the first electrode and the second electrode.

20 Claims, 5 Drawing Sheets

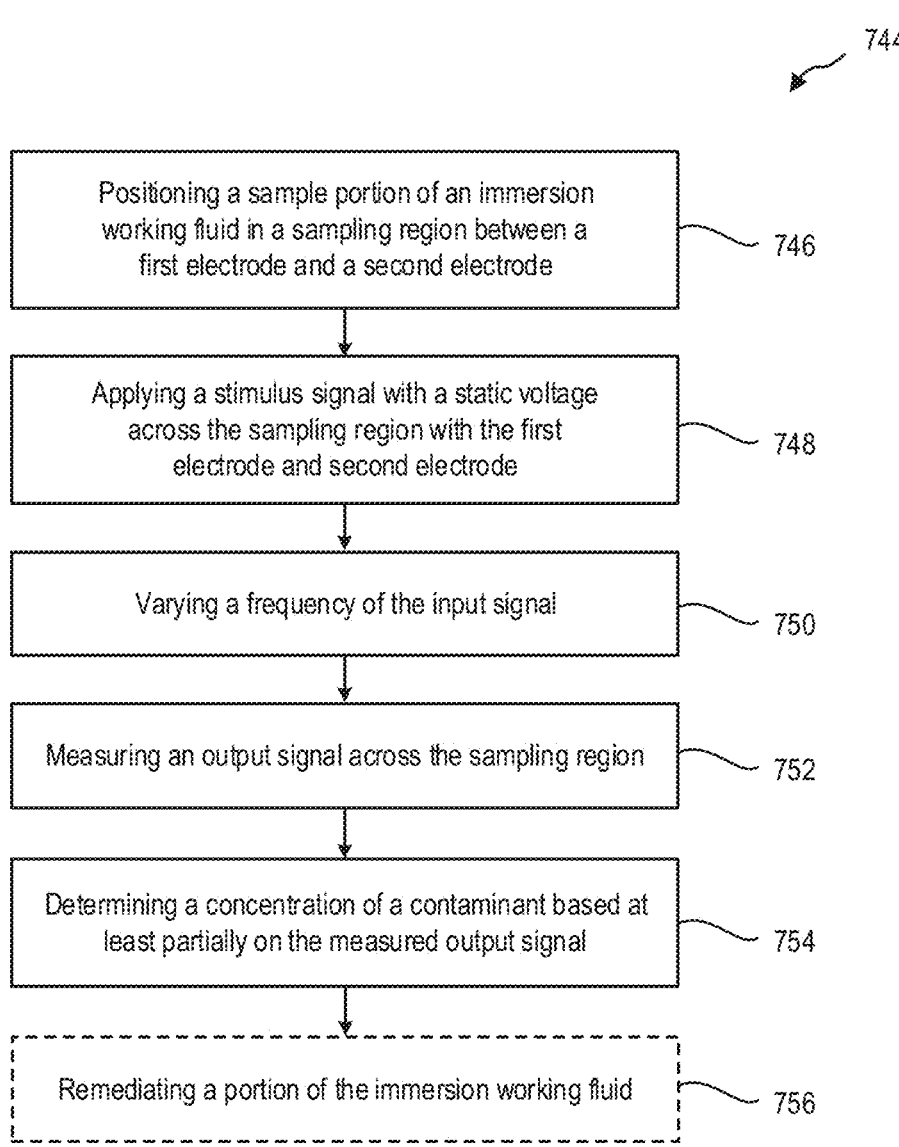

_744_

Positioning a sample portion of an immersion working fluid in a sampling region between a first electrode and a second electrode — 746

Applying a stimulus signal with a static voltage across the sampling region with the first electrode and second electrode — 748

Varying a frequency of the input signal — 750

Measuring an output signal across the sampling region — 752

Determining a concentration of a contaminant based at least partially on the measured output signal — 754

Remediating a portion of the immersion working fluid — 756

FIG. 7

ELECTROCHEMICAL SENSOR FOR SENSING TWO-PHASE COOLING FLUID CONTAMINATION

BACKGROUND

Background and Relevant Art

Computing devices can generate a large amount of heat during use. Immersion cooling allows the temperature of the computing devices and components to be regulated by an immersion fluid. However, contaminations in the working fluid can alter the boiling temperature of the immersion fluid, alter the conductivity of the immersion fluid, cause ion mobilization in the immersion fluid, cause dendritic growth or deposition, and other adverse effects.

BRIEF SUMMARY

In some embodiments, an immersion cooling system includes an immersion tank defining an immersion chamber therein, an immersion working fluid, a first electrode, and a second electrode. The immersion working fluid is positioned at least partially in the immersion chamber. The first electrode is electrically coupled to an electrical power source, and the second electrode is positioned proximate to the first electrode and defines a sampling region therebetween. A sample portion of the immersion working fluid is positioned in the sampling region, and the second electrode is coupled to a microcontroller configured to measure at least a current across the sampling region between the first electrode and the second electrode.

In some embodiments, a method of measuring a liquid working fluid in an immersion cooling system includes circulating an immersion working fluid in the immersion cooling system, positioning a sample portion of an immersion working fluid in a sampling region between a first electrode and a second electrode, applying a stimulus signal with a static voltage across the sampling region with the first electrode and second electrode, varying a frequency of the stimulus signal, measuring an output signal across the sampling region, and determining a first concentration of a contaminant based at least partially on the output signal.

In some embodiments, a method of measuring and remediating a liquid working fluid in an immersion cooling system includes circulating an immersion working fluid in the immersion cooling system, positioning a sample portion of an immersion working fluid in a sampling region between a first electrode and a second electrode, applying a stimulus signal with a static voltage across the sampling region with the first electrode and second electrode, varying a frequency of the stimulus signal, measuring an output signal across the sampling region, determining a concentration of a contaminant based at least partially on the output signal with a microcontroller in communication with the first electrode and second electrode, and remediating the immersion working fluid based at least partially on the concentration of the contaminant using the microcontroller.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the disclosure may be realized and obtained by means of the instruments and combinations particularly pointed out in the appended claims. Features of the present disclosure will become more fully apparent from the following description and appended claims or may be learned by the practice of the disclosure as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example embodiments, the embodiments will be described and explained with additional specificity and detail through the use of the accompanying drawings in which:

FIG. 7 is a flowchart illustrating a method of measuring a contaminant in an immersion cooling system, according to at least one embodiment of the present disclosure.

DETAILED DESCRIPTION

Figure 1:
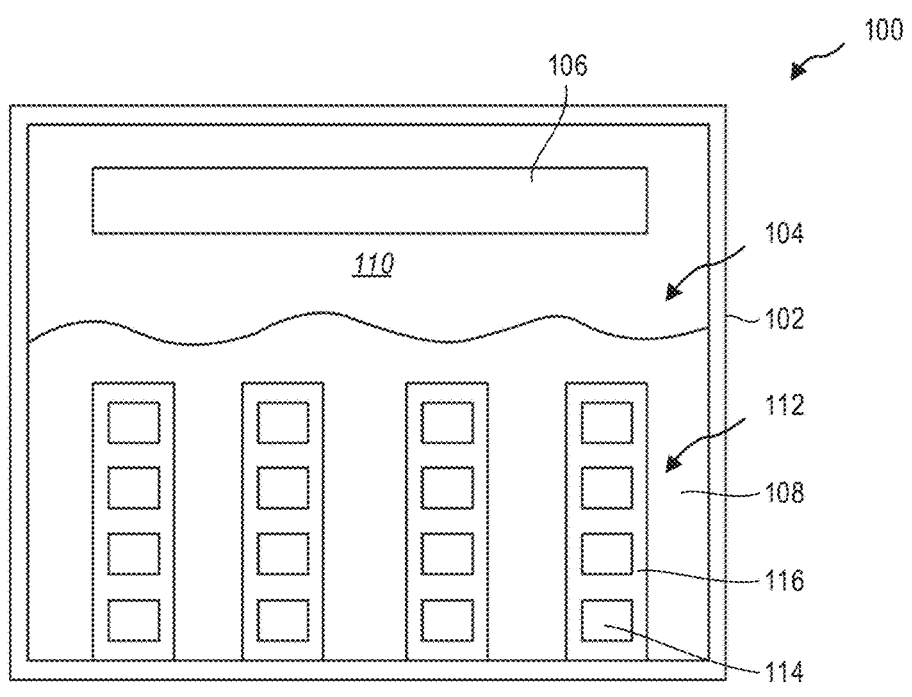
FIG. 1 is a schematic representation of an immersion cooling system, according to at least one embodiment of the present disclosure.

The present disclosure relates generally to systems and methods for thermal management of electronic devices or other heat-generating components. More particularly, the present disclosure relates to systems and methods of detecting contaminants in an immersion cooling system. For example, immersion cooling systems use an immersion working fluid that receives heat from computing devices, electronic components, and other heat-generating components. The immersion working fluid then transports the heat to a heat exchanger to exhaust the heat from the immersion cooling system.

In some examples, contaminants in the immersion working fluid can adversely affect one or more properties of the immersion working fluid, reducing the cooling capacity of the system. In other examples, contaminants in the immersion working fluid can be transported by the immersion working fluid and deposited elsewhere in the immersion cooling system. In at least one example, contaminant ions or particles in the immersion working fluid are deposited on a surface of the heat-generating components, which reduces thermal conductivity from the heat-generating components to the immersion working fluid. In at least another example, contaminant ions or particles in the immersion working fluid are deposited on a surface of the heat-generating components, which results in dendritic growth on the surface of the heat-generating components and may cause an electrical short.

In some embodiments, the immersion working fluid is a two-phase working fluid that receives heat from the heat-generating components by vaporizing. The vaporization can further induce deposition or precipitation of the contaminants. For example, immersion chambers surround the heat-generating components in a liquid working fluid, which conducts heat from the heat-generating components to cool the heat-generating components. As the working fluid absorbs heat from the heat-generating components, the temperature of the working fluid increases. In some embodiments, the hot working fluid can be circulated through the thermal management system to cool the working fluid and/or replace the working fluid with cool working fluid. In some embodiments, the working fluid vaporizes, introducing vapor into the liquid of the working fluid which rises out of the liquid phase, carrying thermal energy away from the heat-generating components in the gas phase via the latent heat of boiling.

In large-scale computing centers, such as cloud-computing centers, data processing centers, data storage centers, or other computing facilities, immersion cooling systems provide an efficient method of thermal management for many computing components under a variety of operating loads. In some embodiments, an immersion cooling system includes a working fluid in an immersion chamber and a heat exchanger to cool the liquid phase and/or a condenser to extract heat from the vapor phase of the working fluid. The heat exchanger may include a condenser that condenses the vapor phase of the working fluid into a liquid phase and returns the liquid working fluid to the immersion chamber. In some embodiments, the liquid working fluid absorbs heat from the heat-generating components, and one or more fluid conduits direct the hot liquid working fluid outside of the immersion chamber to a radiator, heat exchanger, or region of lower temperature to cool the liquid working fluid.

In some embodiments, a high-compute application assigned to and/or executed on the computing devices or systems in the immersion cooling system requires a large amount of thermal management. A working fluid boiling absorbs heat to overcome the latent heat of boiling. The phase change from liquid to vapor, therefore, allows the working fluid to absorb a comparatively large amount of heat with a small associated increase in temperature. Further, the lower density allows the vapor to be removed from the immersion bath efficiently to exhaust the associated heat from the system.

In some embodiments, a thermal management system includes an immersion tank with a two-phase working fluid positioned therein. The two-phase working fluid receives heat from heat-generating components immersed in the liquid working fluid, and the heat vaporizes the working fluid, changing the working fluid from a liquid phase to a vapor phase. The thermal management system includes a condenser, such as described herein, to condense the vapor working fluid back into the liquid phase. In some embodiments, the condenser is in fluid communication with the immersion tank by one or more conduits. In some embodiments, the condenser is positioned inside the immersion tank.

A conventional immersion cooling system 100, shown in FIG. 1, includes an immersion tank 102 containing an immersion chamber 104 and a condenser 106 in the immersion chamber 104. The immersion chamber 104 contains an immersion working fluid that has a liquid working fluid 108 and a vapor working fluid 110 portion. The liquid working fluid 108 creates an immersion bath 112 in which a plurality of heat-generating components 114 are positioned to heat the liquid working fluid 108 on supports 116.

Figure 2:
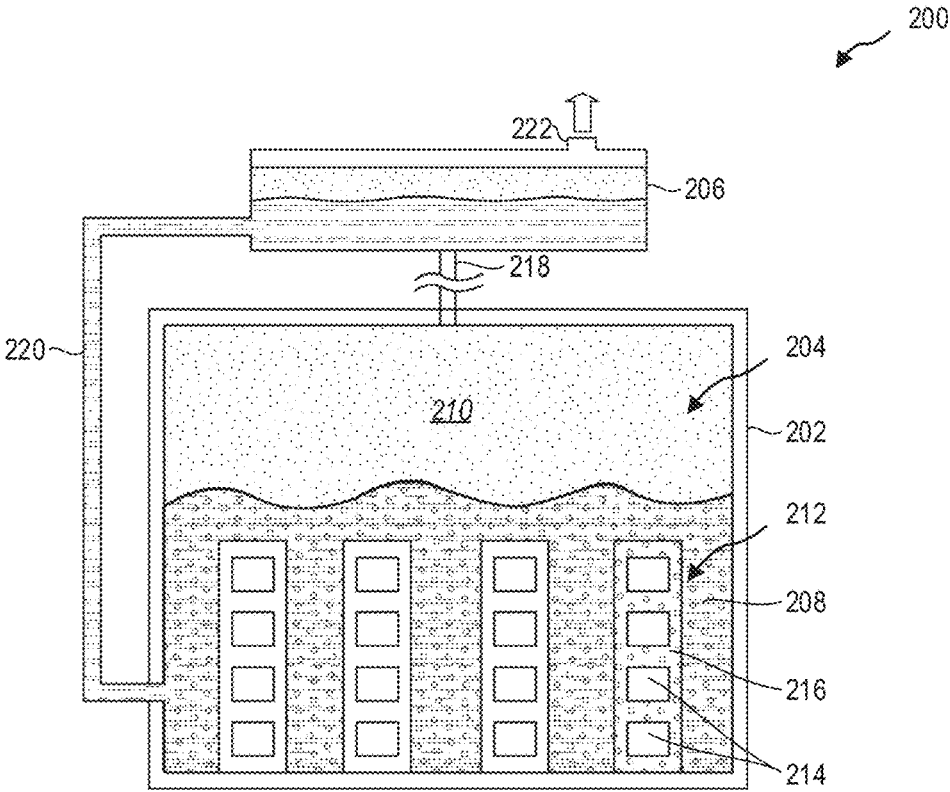
FIG. 2 is a schematic representation of an immersion cooling system with an external condenser, according to at least one embodiment of the present disclosure.

Referring now to FIG. 2, in some embodiments, an immersion cooling system 200 includes an immersion tank 202 defining an immersion chamber 204 with an immersion working fluid positioned therein. An immersion working fluid in the immersion tank 202 has a boiling temperature that is at least partially related to one or more operating properties of the immersion cooling system, the electronic components and/or computing devices in the immersion tank 202, computational or workloads of the electronic components and/or computing devices in the immersion tank 202, external and/or environmental conditions, or other properties that affect the operation of the immersion cooling system 200. As the operating conditions of the immersion cooling system 200 change, the immersion cooling system 200 can change a mixing ratio of the immersion working fluid to change at least one property (such as boiling temperature) of the immersion working fluid.

In some embodiments, the immersion working fluid transitions between a liquid working fluid 208 phase and a vapor working fluid 210 phase to remove heat from hot or heat-generating components 214 in the immersion chamber 204. The liquid working fluid 208 more efficiency receives heat from the heat-generating components 214 and, upon transition to the vapor working fluid 210, the vapor working fluid 210 can be removed from the immersion tank 202, cooled and condensed by the condenser 206 (or other heat exchanger) to extract the heat from the working fluid, and the liquid working fluid 208 can be returned to the liquid immersion bath 212.

In some embodiments, the immersion bath 212 of the liquid working fluid 208 has a plurality of heat-generating components 214 positioned in the liquid working fluid 208. The liquid working fluid 208 surrounds at least a portion of the heat-generating components 214 and other objects or parts attached to the heat-generating components 214. In some embodiments, the heat-generating components 214 are positioned in the liquid working fluid 208 on one or more supports 216. The support 216 may support one or more heat-generating components 214 in the liquid working fluid 208 and allow the working fluid to move around the heat-generating components 214. In some embodiments, the support 216 is thermally conductive to conduct heat from the heat-generating components 214. The support(s) 216 may increase the effective surface area from which the liquid working fluid 208 may remove heat through convective cooling.

In some embodiments, the heat-generating components 214 include electronic or computing components or power supplies. In some embodiments, the heat-generating components 214 include computer devices, such as individual personal computer or server blade computers. In some embodiments, one or more of the heat-generating components 214 includes a heat sink or other device attached to the heat-generating component 214 to conduct away thermal energy and effectively increase the surface area of the heat-generating component 214. In some embodiments, the heat sink of the heat-generating component 214 is a vapor chamber with one or more three-dimensional structures to increase surface area.

As described, conversion of the liquid working fluid 208 to a vapor phase requires the input of thermal energy to overcome the latent heat of vaporization and may be an effective mechanism to increase the thermal capacity of the working fluid and remove heat from the heat-generating components 214. Because the vapor working fluid 210 rises in the liquid working fluid 208, the vapor working fluid 210 can be extracted from the immersion chamber 204 in an upper vapor region of the chamber. A condenser 206 cools part of the vapor working fluid 210 back into a liquid working fluid 208, removing thermal energy from the system and reintroducing the working fluid into the immersion bath 212 of the liquid working fluid 208. The condenser 206 radiates or otherwise dumps the thermal energy from the working fluid into the ambient environment or into a conduit to carry the thermal energy away from the cooling system.

In some embodiments of immersion cooling systems, a liquid-cooled condenser is integrated into the immersion tank and/or the chamber to efficiency remove the thermal energy from the working fluid. In some embodiments, an immersion cooling system 200 for thermal management of computing devices allows at least one immersion tank 202 and/or chamber 204 to be connected to and in fluid communication with an external condenser 206. In some embodiments, an immersion cooling system 200 includes a vapor return line 218 that connects the immersion tank 202 to the condenser 206 and allows vapor working fluid 210 to enter the condenser 206 from the immersion tank 202 and/or chamber 204 and a liquid return conduit 220 that connects the immersion tank 202 to the condenser 206 and allows liquid working fluid 208 to return to the immersion tank 202 and/or chamber 204.

The vapor return line 218 may be colder than the boiling temperature of the working fluid. In some embodiments, a portion of the vapor working fluid 210 condenses in the vapor return line 218. The vapor return line 218 can, in some embodiments, be oriented at an angle such that the vapor return line 218 is non-perpendicular to the direction of gravity. The condensed working fluid can then drain either back to the immersion tank 202 or forward to the condenser 206 depending on the direction of the vapor return line 218 slope. In some embodiments, the vapor return line 218 includes a liquid collection line or valve, like a bleeder valve, that allows the collection and/or return of the condensed working fluid to the immersion tank 202 or condenser 206.

In some examples, an immersion cooling system 200 includes an air-cooled condenser 206. An air-cooled condenser 206 may require fans or pumps to force ambient air over one or more heat pipes or fins to conduct heat from the condenser to the air. In some embodiments, the circulation of immersion working fluid through the immersion cooling system 200 causes liquid working fluid 208 to flow past one or more heat-generating components 214. In the example of a heat-generating component 214 with a vapor chamber heat sink, the dynamics of liquid working fluid 208 may be used to move vapor chamber working fluid within the vapor chamber and/or the boiling of the immersion working fluid by the vapor chamber may drive flow of the immersion working fluid.

In some embodiments, the liquid working fluid receives heat in a cooling volume of working fluid immediately surrounding the heat-generating components. The cooling volume is the region of the working fluid (including both liquid and vapor phases) that is immediately surrounding the heat-generating components and is responsible for the convective cooling of the heat-generating components. In some embodiments, the cooling volume is the volume of working fluid within 5 millimeters (mm) of the heat-generating components.

The immersion working fluid has a boiling temperature below a critical temperature at which the heat-generating components experience thermal damage. The immersion working fluid can thereby receive heat from the heat-generating components to cool the heat-generating components before the heat-generating components experience damage.

For example, the heat-generating components may be computing components that experience damage above 100° Celsius (C). In some embodiments, the boiling temperature of the immersion working fluid is less than a critical temperature of the heat-generating components. In some embodiments, the boiling temperature of the immersion working fluid is less than about 90° C. at 1 atmosphere of pressure. In some embodiments, the boiling temperature of the immersion working fluid is less than about 80° C. at 1 atmosphere of pressure. In some embodiments, the boiling temperature of the immersion working fluid is less than about 70° C. at 1 atmosphere of pressure. In some embodiments, the boiling temperature of the immersion working fluid is less than about 60° C. at 1 atmosphere of pressure. In some embodiments, the boiling temperature of the immersion working fluid is at least about 35° C. at 1 atmosphere of pressure. In some embodiments, the working fluid includes water.

In some embodiments, the working fluid includes glycol. In some embodiments, the working fluid includes a combination of water and glycol. In some embodiments, the working fluid includes an aqueous solution. In some embodiments, the working fluid includes an electronic liquid, such as FC-72 available from 3M, or similar nonconductive fluids. In some embodiments, the heat-generating components, supports, or other elements of the immersion cooling system positioned in the working fluid have nucleation sites on a surface thereof that promote the nucleation of vapor bubbles of the working fluid at or below the boiling temperature of the working fluid.

In some embodiments, sensors according to the present disclosure detect and/or measure the presence of one or more contaminants in the immersion working fluid. In some embodiments, the immersion working fluid is a two-phase working fluid that boils during operations of the immersion cooling system. In some embodiments, the immersion working fluid is a single-phase working fluid that remains in a liquid phase through the immersion cooling system operations. While detecting the presence of contaminants in a single-phase immersion working fluid is beneficial to the operation of a single-phase immersion cooling system, two-phase working fluids experience additional concerns with effects on the boiling temperature of the immersion working fluid and increased deposition rates of contaminants on components in the immersion chamber due to boiling of the working fluid.

Figure 3:
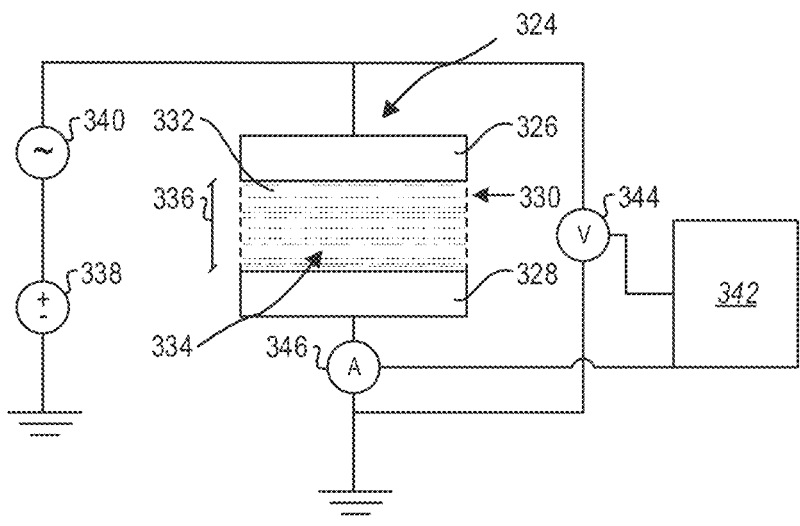
FIG. 3 is an electrical diagram of an electrochemical sensor, according to at least one embodiment of the present disclosure.

FIG. 3 is a schematic representation of an electrochemical sensor 324 according to at least some embodiments of the present disclosure configured to measure ionic contaminants in solution in the immersion working fluid. The sensor 324 includes a first electrode 326 and a second electrode 328 that define a sampling region 330 therebetween. For example, a first sampling surface 332 of the first electrode 326 and a second sampling surface 334 of the second electrode 328 may be substantially parallel to one another with a constant electrode gap 336. In other examples, at least a portion of the first sampling surface 332 of the first electrode 326 and the second sampling surface 334 of the second electrode 328 are not parallel with one another, and the electrode gap 336 is defined by the portion of the first sampling surface 332 closest to the second sampling surface 334.

In some embodiments, the electrode gap 336 is less than 100 microns. In some embodiments, the electrode gap 336 is less than 50 microns. In some embodiments, the electrode gap 336 is less than 20 microns. In some embodiments, the electrode gap 336 is less than 10 microns. A smaller electrode gap 336 allows for lower voltages and/or amperages needed across the sampling region 330, however the immersion working fluid may include larger particles of debris that may adversely affect the sensor 324 if the larger particles enter the sampling region.

The sensor 324 may further include an electrical power source including direct current (DC) source 338 and an alternating current (AC) stimulus 340 with variable amplitude and frequency. The sensor 324 will apply the current and voltage selected from the DC source 338 and the AC stimulus 340 to the sample portion of the immersion working fluid in the sampling region 330.

A measurement system (configured to measure voltage and current) is connected across the sampling region 330. The measurement system includes a microcontroller 342 configured to receive voltage measurements from a voltmeter 344 and current measurements from an ammeter 346. The stimulus signal provided by the DC source 338 and the AC stimulus 340 driving the electrochemical signal consists of static voltage coupled with a small amplitude swept sine wave. Different contaminants in the immersion working fluid will have different static voltages. By sweeping the stimulus signal provided by the DC source 338 and the AC stimulus 340 through a range of voltages, the electrochemical response at and/or around the static voltage can be measured.

Figure 4:
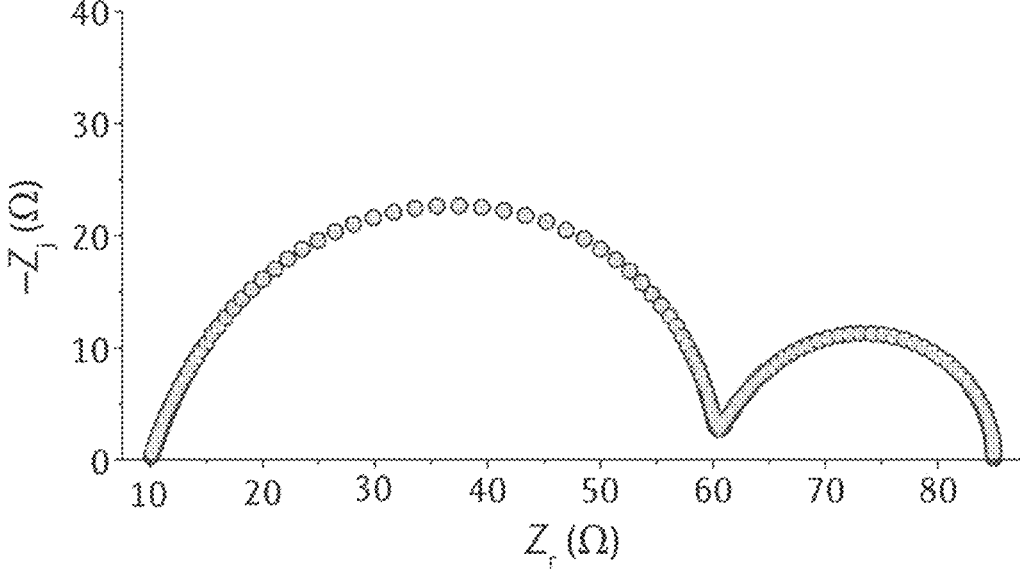
FIG. 4 is an example contour measured by the electrochemical sensor of FIG. 3, according to at least one embodiment of the present disclosure.

The voltage across the electrochemical cell and the current through it are measured during the frequency sweep. These signals are sampled by an analog to digital converter and stored in memory as complex numbers with both signal magnitude and phase measured. The resultant complex voltage and current measurements at each frequency point are processed to create a complex impedance value at that frequency. The resulting two-dimensional impedance data points are processed, for example, by the microcontroller 342, to convert the measured magnitude and phase into real and imaginary coordinates. These points form a contour, such as shown in FIG. 4.

In some embodiments, multiple contours will be captured over time to track and/or correlate the evolution of the shape of the contour based on changes in concentrations and/or stimulus signal. A machine learning (ML) model may be trained based on known concentrations of one or more contaminants to allow the ML model to recognize or calculate concentrations of the one or more contaminants and/or other contaminants in an immersion working fluid relative to a stimulus signal.

Figure 5:
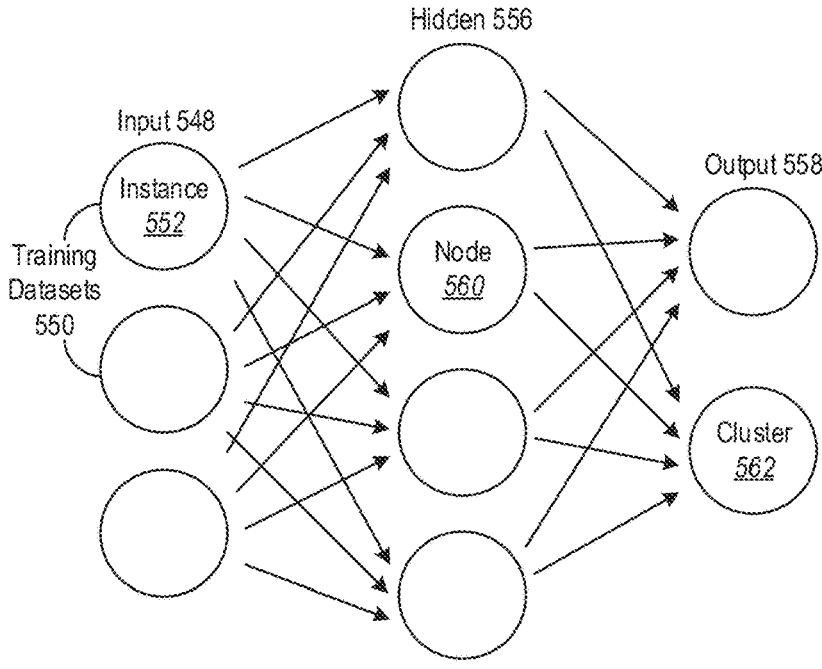
FIG. 5 is a schematic diagram of a machine learning model, according to at least one embodiment of the present disclosure.

FIG. 5 is a schematic representation of an ML model that may be used with one or more embodiments of systems and methods described herein. As used herein, a "machine learning model" refers to a computer algorithm or model (e.g., a classification model, a regression model, a language model, an object detection model) that can be tuned (e.g., trained) based on training input to approximate unknown functions. For example, an ML model may refer to a neural network or other machine learning algorithm or architecture that learns and approximates complex functions and generate outputs based on a plurality of inputs provided to the machine learning model. In some embodiments, an ML system, model, or neural network described herein is an artificial neural network. In some embodiments, an ML system, model, or neural network described herein is a convolutional neural network. In some embodiments, an ML system, model, or neural network described herein is a recurrent neural network. In at least one embodiment, an ML system, model, or neural network described herein is a Bayes classifier. As used herein, a "machine learning system" may refer to one or multiple ML models that cooperatively generate one or more outputs based on corresponding inputs. For example, an ML system may refer to any system architecture having multiple discrete ML components that consider different kinds of information or inputs.

As used herein, an "instance" refers to an input object that may be provided as an input to an ML system to use in generating an output, such as a species of contaminant present, a concentration of contaminant present, or a rate of change in a contaminant present. For example, an instance may refer to any event in which the contaminant is present. For example, a first contour or other measurement received at the microcontroller may be related to a first contaminant being present in the sample portion of the immersion working fluid. In another example, a second contour or other measurement received at the microcontroller may be related to a second contaminant being present in the sample portion of the immersion working fluid. In another example, a change in a contour or other measurement received at the microcontroller may be related to an increasing concentration of a contaminant in the sample portion of the immersion working fluid.

In some embodiments, the machine learning system has a plurality of layers with an input layer 548 configured to receive at least one input training dataset 550 or input training instance 552 and an output layer 558, with a plurality of additional or hidden layers 556 therebetween. The training datasets can be input into the ML system to train the ML system and identify individual and combinations of contaminants or other attributes of the training instances that allow the microcontroller to identify concentrations of known or unknown contaminants.

In some embodiments, the machine learning system can receive multiple training datasets concurrently and learn from the different training datasets simultaneously.

In some embodiments, the machine learning system includes a plurality of machine learning models that operate together. Each of the machine learning models has a plurality of hidden layers between the input layer and the output layer. The hidden layers have a plurality of input nodes (e.g., nodes 560), where each of the nodes operates on the received inputs from the previous layer. In a specific example, a first hidden layer has a plurality of nodes and each of the nodes performs an operation on each instance from the input layer. Each node of the first hidden layer provides a new input into each node of the second hidden layer, which, in turn, performs a new operation on each of those inputs. The nodes of the second hidden layer then passes outputs, such as identified clusters 562, to the output layer.

In some embodiments, each of the nodes 560 has a linear function and an activation function. The linear function may attempt to optimize or approximate a solution with a line of best fit, such as reduced power cost or reduced latency. The activation function operates as a test to check the validity of the linear function. In some embodiments, the activation function produces a binary output that determines whether the output of the linear function is passed to the next layer of the machine learning model. In this way, the machine learning system can limit and/or prevent the propagation of poor fits to the data and/or non-convergent solutions.

The machine learning model includes an input layer that receives at least one training dataset. In some embodiments, at least one machine learning model uses supervised training. In some embodiments, at least one machine learning model uses unsupervised training. Unsupervised training can be used to draw inferences and find patterns or associations from the training dataset(s) without known outputs. In some embodiments, unsupervised learning can identify clusters of similar labels or characteristics for a variety of training instances and allow the machine learning system to extrapolate the performance of instances with similar characteristics.

In some embodiments, semi-supervised learning can combine benefits from supervised learning and unsupervised learning. As described herein, the machine learning system can identify associated labels (such as known contaminants or concentrations of contaminants) or characteristic between instances, which may allow a training dataset with known outputs and a second training dataset including more general input information to be fused. Unsupervised training can allow the machine learning system to cluster the instances from the second training dataset without known outputs and associate the clusters with known outputs from the first training dataset.

Figure 6:
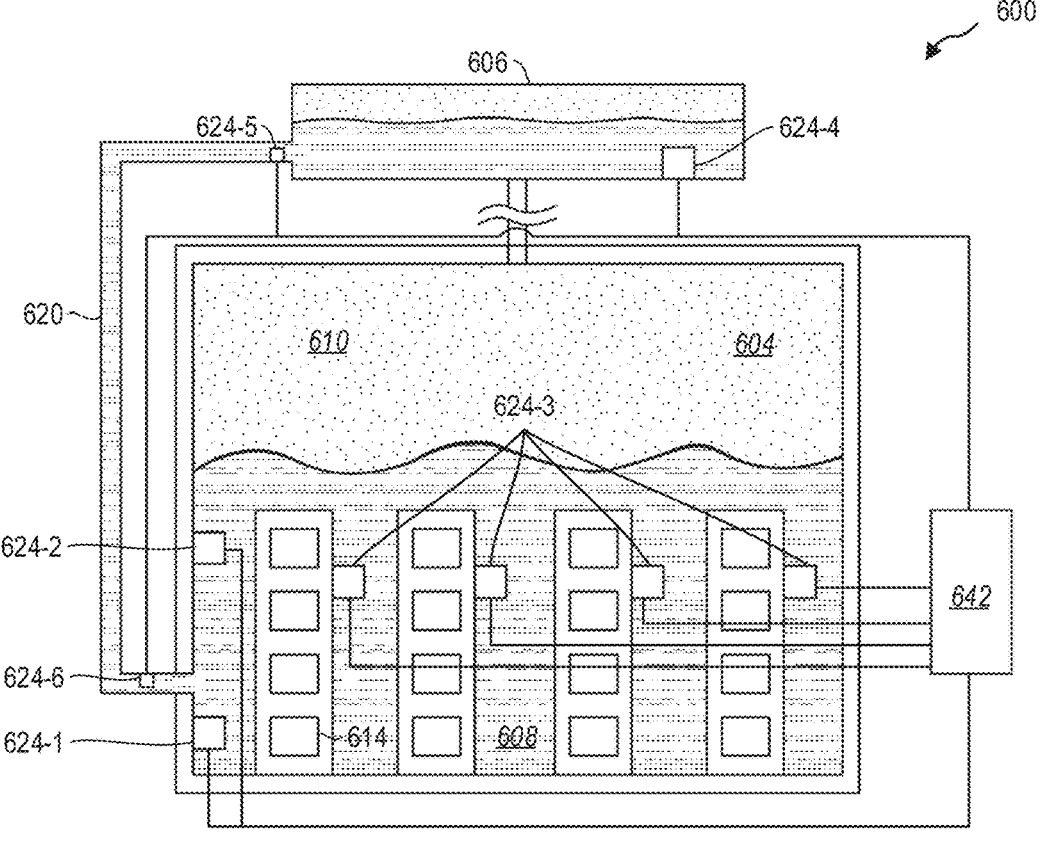
FIG. 6 is a schematic representation of an immersion cooling system with a plurality of electrochemical sensors, according to at least one embodiment of the present disclosure.

FIG. 6 is a system diagram of an immersion cooling system 600 with a plurality of electrochemical sensors 624-1, 624-2, 624-3, 624-4, 624-5, 624-6 positioned in contact with a liquid phase of the immersion working fluid (e.g., liquid working fluid 608). In some embodiments, the immersion cooling system 600 includes the electrochemical sensors 624-1, 624-2, 624-3, 624-4, 624-5, 624-6 positioned at variety of locations in the immersion cooling system 600. For example, a first electrochemical sensor 624-1 may be positioned in a lower portion of the immersion chamber 604 with the heat-generating components 614. The first electrochemical sensor 624-1 may be positioned to measure one or more contaminants that are present in the liquid working fluid 608 in contact with the heat-generating components 614. As described herein, a two-phase immersion working fluid presents an increased risk of dendritic growth during vaporization of the liquid working fluid 608 in contact with the heat-generating components 614. For at least that reason, a first electrochemical sensor 624-1 positioned to measure contaminants proximate to the heat-generating components 614 may be desirable.

In another example, a second electrochemical sensor 624-2 may be positioned proximate a liquid-vapor boundary between the liquid working fluid 608 and the vapor working fluid 610. The second electrochemical sensor 624-2 may measure a contaminant concentration at or near the top of the liquid working fluid 608 in the immersion chamber 604 to provide a relative concentration between the lower portion proximate the first electrochemical sensor 624-1 and the top portion, for example, to aide in determining a source or source location of the contaminants in the liquid working fluid 608.

In yet another example, one or more third electrochemical sensors 624-3 may be positioned proximate the heat-generating components 614, such as within a cooling volume proximate a heat-generating component 614. The one or more third electrochemical sensors 624-3 may measure the presence of the contaminants proximate the heat source in the immersion chamber 604 and, therefore, the amount of contaminants that are present in the boiling portion of the liquid working fluid 608. As described herein, the liquid working fluid 608 boiling can increase the rate of deposition of the contaminant ions and/or rate of dendritic growth on the heat-generating components 614, such as on pins or interconnects of a computing device. Measuring the contaminants proximate to the heat-generating components 614 can provide the microcontroller 642 with information to predict a risk of damage or failure to the heat-generating components 614.

In a further example, a fourth electrochemical sensor 624-4 may be positioned in or proximate to the condenser 606. In some embodiments, the condenser 606 condenses the vapor working fluid 610 into a condensate liquid working fluid 608 in or contacting the condenser 606. In at least one example, the liquid working fluid 608, upon boiling, converts into a vapor working fluid 610 that does not contain the contaminant ions, and the condensate liquid working fluid 608 in or on the condenser 606 does not contain the contaminant ions, unless the at least some contaminant ions in the liquid working fluid 608 originate from the condenser 606. Measuring the contaminant concentrations at or in the condenser 606 with a fourth electrochemical sensor 624-4 may provide the microcontroller 642 with information related to a source or source location of the contaminant ions in the liquid working fluid 608.

In a yet further example, a fifth electrochemical sensor 624-5 is located at a first end of the return conduit 620 of the immersion cooling system 600 and/or a sixth electrochemical sensor 624-6 positioned at a second end of the return conduit 620. In some embodiments, the immersion cooling system 600 delivers condensate liquid working fluid 608 from the condenser 606 to the immersion chamber 604 through the return conduit 620. By detecting a contaminant and/or measuring a contaminant level at one or more locations in the return conduit 620, the fifth electrochemical sensor 624-5 and/or sixth electrochemical sensor 624-6 can provide the microcontroller 642 with information related to a source or source location of the contaminant ions in the liquid working fluid 608.

In some embodiments, the microcontroller 642 calculates a concentration of contaminants in the liquid working fluid 608 at one or more locations in the immersion cooling system 600. The microcontroller 642 or other control plane of the immersion cooling system may suggest or automatically enact remediation to the liquid working fluid to remove contaminants from the liquid working fluid 608 and/or replace the contaminated liquid working fluid 608 with new, uncontaminated working fluid.

FIG. 7 is a flowchart illustrating an embodiment of a method 744 of measuring and remediating a liquid working fluid in an immersion cooling system. In some embodiments, the method 744 includes positioning a sample portion of an immersion working fluid in a sampling region between a first electrode and a second electrode at 746 and applying a stimulus signal with a static voltage across the sampling region with the first electrode and second electrode at 748. The method 744 includes varying a frequency of the input signal at 750 and measuring an output signal across the sampling region at 752 as described, such as in relation to FIG. 3 and FIG. 4.

In some embodiments, the method 744 is performed inline while the immersion cooling system is operating. For example, the sample portion of the immersion working fluid of 746 may be a portion of the liquid working fluid in an immersion chamber, in a condenser, in a return conduit, or other portion of the immersion cooling system. Sampling at multiple times and/or at multiple locations in the immersion cooling system can allow a microcontroller to determine a concentration of a contaminant based at least partially on the measured output signal at 754.

In some embodiments, the method 744 optionally includes remediating a portion of the immersion working fluid at 756. For example, remediating a portion of the immersion working fluid may include changing one or more filters in the immersion cooling system, such as proximate an inlet or outlet of the condenser, proximate an inlet or outlet of the immersion tank or chamber, proximate an inlet or outlet of a return conduit, or at other locations in the immersion cooling system.

In another example, remediating a portion of the immersion working fluid may include adding uncontaminated immersion working fluid to the immersion cooling system, such as opening a valve to add uncontaminated immersion working fluid to the immersion cooling system. Adding uncontaminated immersion working fluid to the immersion cooling system may dilute the contaminant ions in the existing immersion working fluid, reducing effects of the contaminant ions on one or more properties of the immersion working fluid, such as conductivity, boiling temperature, or other properties. In other example, diluting the contaminant ions in the immersion working fluid may reduce a deposition rate and reduce dendritic growth. In at least one embodiment, adding uncontaminated immersion working fluid to the immersion cooling system includes opening a valve to allow the uncontaminated immersion working fluid to flow from a reservoir through the valve into the immersion cooling system. For example, the valve may be controlled by the microcontroller, and the microcontroller may open the valve at least partially based on the measured output signal(s).

In yet another example, remediating a portion of the immersion working fluid may include replacing contaminated immersion working fluid with an uncontaminated immersion working fluid. Replacing contaminated immersion working fluid with an uncontaminated immersion working fluid may include opening at least a first valve to drain a portion of the contaminated immersion working fluid from the immersion cooling system and opening at least a second valve to allow uncontaminated immersion working fluid to flow from a reservoir through the valve into the immersion cooling system. In at least one embodiment, the valves may be controlled by the microcontroller, and the microcontroller may open the valves at least partially based on the measured output signal(s).

Figure 8:
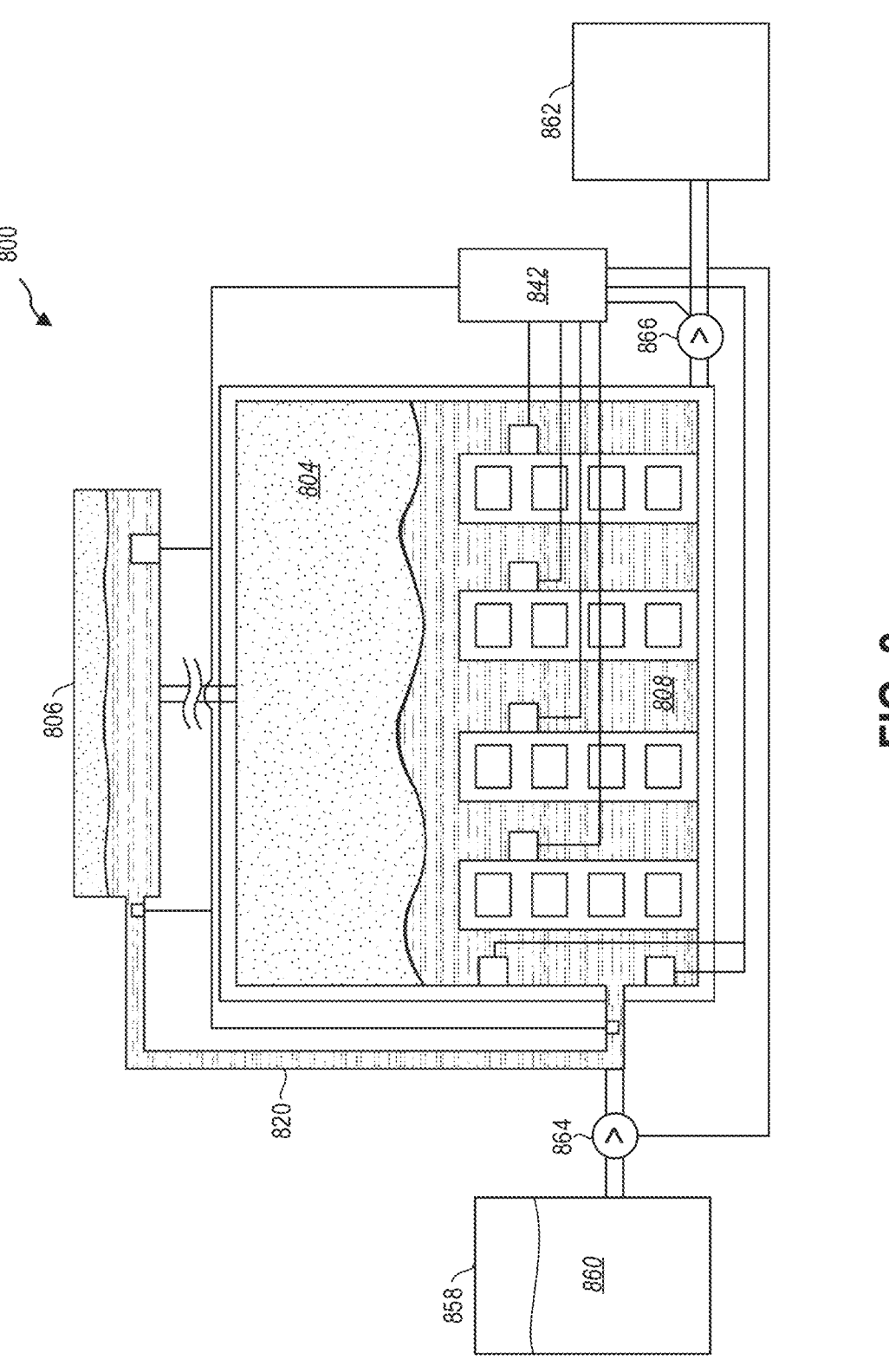
FIG. 8 is a schematic representation of an immersion cooling system with remediation features, according to at least one embodiment of the present disclosure.

FIG. 8 is a schematic representation of an embodiment of an immersion cooling system 800 with remediation capabilities. For example, the immersion cooling system 800 may include a reservoir 858 containing an uncontaminated immersion working fluid 860 and a collection tank 862 configured to capture at least a portion of the contaminated liquid working fluid 808. In some embodiments, the reservoir 858 is connected to the return conduit 820 or other inlet to the immersion chamber 804 to introduce the uncontaminated immersion working fluid 860 into the immersion chamber 804. In other examples, the reservoir 852 may be connected to the immersion chamber 804 directly or by a dedicated conduit, or the reservoir 852 may be connected to the condenser 806 to deliver the uncontaminated immersion working fluid 860 into the immersion cooling system 800 via the condenser 806.

In some embodiments, a first valve 864 controls a flow of the uncontaminated immersion working fluid 860 into the immersion cooling system 800. The first valve 864 may be controlled by the microcontroller 842. In other embodiments, the first valve 864 may be controlled by another control plane that receives contaminant and/or contaminant concentration information from the microcontroller 842.

A collection tank 862 may be connected to the immersion cooling system 800 by a second valve 866. In some embodiments, the collection tank 862 is connected to the return conduit 820 or other conduit of the immersion chamber 804 to receive contaminated liquid working fluid 808 from the immersion chamber 804. In other examples, the collection tank 862 may be connected to the immersion chamber 804 directly or by a dedicated conduit, or the collection tank 862 may be connected to the condenser 806 to receive the contaminated liquid working fluid 808 from the immersion cooling system 800 via the condenser 806.

In some embodiments, the second valve 866 controls a flow of the contaminated liquid working fluid 808 into the immersion cooling system 800. The second valve 866 may be controlled by the microcontroller 842. In other embodiments, the second valve 866 may be controlled by another control plane that receives contaminant and/or contaminant concentration information from the microcontroller 842. In at least one embodiment, the microcontroller 842 or other control plane opens the first valve 864 and the second valve 866 at least partially simultaneously (e.g., a period of time when the first valve 864 is open at least partially overlaps a period of time when the second valve 866 is open) to introduce uncontaminated immersion working fluid 860 into the immersion cooling system 800 from the reservoir 858 while at least a portion of the contaminated liquid working fluid 808 is removed into the collection tank 862.

INDUSTRIAL APPLICABILITY

The present disclosure relates generally to systems and methods for thermal management of electronic devices or other heat-generating components. More particularly, the present disclosure relates to systems and methods of detecting contaminants in an immersion cooling system. For example, immersion cooling systems use an immersion working fluid that receives heat from computing devices, electronic components, and other heat-generating components. The immersion working fluid then transports the heat to a heat exchanger to exhaust the heat from the immersion cooling system.

In some examples, contaminants in the immersion working fluid can adversely affect one or more properties of the immersion working fluid, reducing the cooling capacity of the system. In other examples, contaminants in the immersion working fluid can be transported by the immersion working fluid and deposited elsewhere in the immersion cooling system. In at least one example, contaminant ions or particles in the immersion working fluid are deposited on a surface of the heat-generating components, which reduces thermal conductivity from the heat-generating components to the immersion working fluid. In at least another example, contaminant ions or particles in the immersion working fluid are deposited on a surface of the heat-generating components, which results in dendritic growth on the surface of the heat-generating components and may cause an electrical short.

In some embodiments, the immersion working fluid is a two-phase working fluid that receives heat from the heat-generating components by vaporizing. The vaporization can further induce deposition or precipitation of the contaminants. For example, immersion chambers surround the heat-generating components in a liquid working fluid, which conducts heat from the heat-generating components to cool the heat-generating components. As the working fluid absorbs heat from the heat-generating components, the temperature of the working fluid increases. In some embodiments, the hot working fluid can be circulated through the thermal management system to cool the working fluid and/or replace the working fluid with cool working fluid. In some embodiments, the working fluid vaporizes, introducing vapor into the liquid of the working fluid which rises out of the liquid phase, carrying thermal energy away from the heat-generating components in the gas phase via the latent heat of boiling.

In large-scale computing centers, such as cloud-computing centers, data processing centers, data storage centers, or other computing facilities, immersion cooling systems provide an efficient method of thermal management for many computing components under a variety of operating loads. In some embodiments, an immersion cooling system includes a working fluid in an immersion chamber and a heat exchanger to cool the liquid phase and/or a condenser to extract heat from the vapor phase of the working fluid. The heat exchanger may include a condenser that condenses the vapor phase of the working fluid into a liquid phase and returns the liquid working fluid to the immersion chamber. In some embodiments, the liquid working fluid absorbs heat from the heat-generating components, and one or more fluid conduits direct the hot liquid working fluid outside of the immersion chamber to a radiator, heat exchanger, or region of lower temperature to cool the liquid working fluid.

In some embodiments, a high-compute application assigned to and/or executed on the computing devices or systems in the immersion cooling system requires a large amount of thermal management. A working fluid boiling absorbs heat to overcome the latent heat of boiling. The phase change from liquid to vapor, therefore, allows the working fluid to absorb a comparatively large amount of heat with a small associated increase in temperature. Further, the lower density allows the vapor to be removed from the immersion bath efficiently to exhaust the associated heat from the system.

In some embodiments, a thermal management system includes an immersion tank with a two-phase working fluid positioned therein. The two-phase working fluid receives heat from heat-generating components immersed in the liquid working fluid, and the heat vaporizes the working fluid, changing the working fluid from a liquid phase to a vapor phase. The thermal management system includes a condenser, such as described herein, to condense the vapor working fluid back into the liquid phase. In some embodiments, the condenser is in fluid communication with the immersion tank by one or more conduits. In some embodiments, the condenser is positioned inside the immersion tank.

Some conventional immersion cooling systems includes an immersion tank containing an immersion chamber and a condenser in the immersion chamber. The immersion chamber contains an immersion working fluid that has a liquid working fluid and a vapor working fluid portion. The liquid working fluid creates an immersion bath in which a plurality of heat-generating components are positioned to heat the liquid working fluid on supports.

In some embodiments, an immersion cooling system includes an immersion tank defining an immersion chamber with an immersion working fluid positioned therein. An immersion working fluid in the immersion tank has a boiling temperature that is at least partially related to one or more operating properties of the immersion cooling system, the electronic components and/or computing devices in the immersion tank, computational or workloads of the electronic components and/or computing devices in the immersion tank, external and/or environmental conditions, or other properties that affect the operation of the immersion cooling system.

In some embodiments, the immersion working fluid transitions between a liquid working fluid phase and a vapor working fluid phase to remove heat from hot or heat-generating components in the immersion chamber. The liquid working fluid more efficiency receives heat from the heat-generating components and, upon transition to the vapor working fluid, the vapor working fluid can be removed from the immersion tank, cooled and condensed by the condenser (or other heat exchanger) to extract the heat from the working fluid, and the liquid working fluid can be returned to the liquid immersion bath.

In some embodiments, the immersion bath of the liquid working fluid has a plurality of heat-generating components positioned in the liquid working fluid. The liquid working fluid surrounds at least a portion of the heat-generating components and other objects or parts attached to the heat-generating components. In some embodiments, the heat-generating components are positioned in the liquid working fluid on one or more supports. The support may support one or more heat-generating components in the liquid working fluid and allow the working fluid to move around the heat-generating components. In some embodiments, the support is thermally conductive to conduct heat from the heat-generating components. The support(s) may increase the effective surface area from which the liquid working fluid may remove heat through convective cooling.

In some embodiments, the heat-generating components include electronic or computing components or power supplies. In some embodiments, the heat-generating components include computer devices, such as individual personal computer or server blade computers. In some embodiments, one or more of the heat-generating components includes a heat sink or other device attached to the heat-generating component to conduct away thermal energy and effectively increase the surface area of the heat-generating component. In some embodiments, the heat sink of the heat-generating component is a vapor chamber with one or more three-dimensional structures to increase surface area.

As described, conversion of the liquid working fluid to a vapor phase requires the input of thermal energy to overcome the latent heat of vaporization and may be an effective mechanism to increase the thermal capacity of the working fluid and remove heat from the heat-generating components. Because the vapor working fluid rises in the liquid working fluid, the vapor working fluid can be extracted from the immersion chamber in an upper vapor region of the chamber. A condenser cools part of the vapor working fluid back into a liquid working fluid, removing thermal energy from the system and reintroducing the working fluid into the immersion bath of the liquid working fluid. The condenser radiates or otherwise dumps the thermal energy from the working fluid into the ambient environment or into a conduit to carry the thermal energy away from the cooling system.

In some embodiments of immersion cooling systems, a liquid-cooled condenser is integrated into the immersion tank and/or the chamber to efficiency remove the thermal energy from the working fluid. In some embodiments, an immersion cooling system for thermal management of computing devices allows at least one immersion tank and/or chamber to be connected to and in fluid communication with an external condenser. In some embodiments, an immersion cooling system includes a vapor return line that connects the immersion tank to the condenser and allows vapor working fluid to enter the condenser from the immersion tank and/or chamber and a liquid return conduit that connects the immersion tank to the condenser and allows liquid working fluid to return to the immersion tank and/or chamber.

The vapor return line may be colder than the boiling temperature of the working fluid. In some embodiments, a portion of the vapor working fluid condenses in the vapor return line. The vapor return line can, in some embodiments, be oriented at an angle such that the vapor return line is non-perpendicular to the direction of gravity. The condensed working fluid can then drain either back to the immersion tank or forward to the condenser depending on the direction of the vapor return line slope. In some embodiments, the vapor return line includes a liquid collection line or valve, like a bleeder valve, that allows the collection and/or return of the condensed working fluid to the immersion tank or condenser.

In some examples, an immersion cooling system includes an air-cooled condenser. An air-cooled condenser may require fans or pumps to force ambient air over one or more heat pipes or fins to conduct heat from the condenser to the air. In some embodiments, the circulation of immersion working fluid through the immersion cooling system causes liquid working fluid to flow past one or more heat-generating components. In the example of a heat-generating component with a vapor chamber heat sink, the dynamics of liquid working fluid may be used to move vapor chamber working fluid within the vapor chamber and/or the boiling of the immersion working fluid by the vapor chamber may drive flow of the immersion working fluid.

In some embodiments, the liquid working fluid receives heat in a cooling volume of working fluid immediately surrounding the heat-generating components. The cooling volume is the region of the working fluid (including both liquid and vapor phases) that is immediately surrounding the heat-generating components and is responsible for the convective cooling of the heat-generating components. In some embodiments, the cooling volume is the volume of working fluid within 5 millimeters (mm) of the heat-generating components.

The immersion working fluid has a boiling temperature below a critical temperature at which the heat-generating components experience thermal damage. The immersion working fluid can thereby receive heat from the heat-generating components to cool the heat-generating components before the heat-generating components experience damage.

For example, the heat-generating components may be computing components that experience damage above 100° Celsius (C). In some embodiments, the boiling temperature of the immersion working fluid is less than a critical temperature of the heat-generating components. In some embodiments, the boiling temperature of the immersion working fluid is less than about 90° C. at 1 atmosphere of pressure. In some embodiments, the boiling temperature of the immersion working fluid is less than about 80° C. at 1 atmosphere of pressure. In some embodiments, the boiling temperature of the immersion working fluid is less than about 70° C. at 1 atmosphere of pressure. In some embodiments, the boiling temperature of the immersion working fluid is less than about 60° C. at 1 atmosphere of pressure. In some embodiments, the boiling temperature of the immersion working fluid is at least about 35° C. at 1 atmosphere of pressure. In some embodiments, the working fluid includes water.

In some embodiments, the working fluid includes glycol. In some embodiments, the working fluid includes a combination of water and glycol. In some embodiments, the working fluid includes an aqueous solution. In some embodiments, the working fluid includes an electronic liquid, such as FC-72 available from 3M, or similar non-conductive fluids. In some embodiments, the heat-generating components, supports, or other elements of the immersion cooling system positioned in the working fluid have nucleation sites on a surface thereof that promote the nucleation of vapor bubbles of the working fluid at or below the boiling temperature of the working fluid.

In some embodiments, sensors according to the present disclosure detect and/or measure the presence of one or more contaminants in the immersion working fluid. In some embodiments, the immersion working fluid is a two-phase working fluid that boils during operations of the immersion cooling system. In some embodiments, the immersion working fluid is a single-phase working fluid that remains in a liquid phase through the immersion cooling system operations. While detecting the presence of contaminants in a single-phase immersion working fluid is beneficial to the operation of a single-phase immersion cooling system, two-phase working fluids experience additional concerns with effects on the boiling temperature of the immersion working fluid and increased deposition rates of contaminants on components in the immersion chamber due to boiling of the working fluid.

In some embodiments, an electrochemical sensor according to at least some embodiments of the present disclosure is configured to measure ionic contaminants in solution in the immersion working fluid. The sensor includes a first electrode and a second electrode that define a sampling region therebetween. For example, a first sampling surface of the first electrode and a second sampling surface of the second electrode may be substantially parallel to one another with a constant electrode gap. In other examples, at least a portion of the first sampling surface of the first electrode and the second sampling surface of the second electrode are not parallel with one another, and the electrode gap is defined by the portion of the first sampling surface closest to the second sampling surface.

In some embodiments, the electrode gap is less than 100 microns. In some embodiments, the electrode gap is less than 50 microns. In some embodiments, the electrode gap is less than 20 microns. In some embodiments, the electrode gap is less than 10 microns. A smaller electrode gap allows for lower voltages and/or amperages needed across the sampling region, however the immersion working fluid may include larger particles of debris that may adversely affect the sensor if the larger particles enter the sampling region.

The sensor may further include an electrical power source including a direct current (DC) source and an alternating current (AC) stimulus with variable amplitude and frequency. The sensor will apply the current and voltage selected from the DC source and the AC stimulus to the sample portion of the immersion working fluid in the sampling region.

A measurement system (configured to measure voltage and current) is connected across the sampling region. The measurement system includes a microcontroller configured to receive voltage measurements from a voltmeter and current measurements from an ammeter. The stimulus signal provided by the DC source and the AC stimulus driving the electrochemical signal consists of static voltage coupled with a small amplitude swept sine wave. Different contaminants in the immersion working fluid will have different static voltages. By sweeping the stimulus signal provided by the DC source and the AC stimulus through a range of voltages, the electrochemical response at and/or around the static voltage can be measured.

The voltage across the electrochemical cell and the current through it are measured during the frequency sweep. These signals are sampled by an analog to digital converter and stored in memory as complex numbers with both signal magnitude and phase measured. The resultant complex voltage and current measurements at each frequency point are processed to create a complex impedance value at that frequency. The resulting two-dimensional impedance data points are processed, for example, by the microcontroller, to convert the measured magnitude and phase into real and imaginary coordinates. These points form a contour.

In some embodiments, multiple contours will be captured over time to track and/or correlate the evolution of the shape of the contour based on changes in concentrations and/or stimulus signal. A machine learning (ML) model may be trained based on known concentrations of one or more contaminants to allow the ML model to recognize or calculate concentrations of the one or more contaminants and/or other contaminants in an immersion working fluid relative to a stimulus signal.

As used herein, a "machine learning model" refers to a computer algorithm or model (e.g., a classification model, a regression model, a language model, an object detection model) that can be tuned (e.g., trained) based on training input to approximate unknown functions. For example, an ML model may refer to a neural network or other machine learning algorithm or architecture that learns and approximates complex functions and generate outputs based on a plurality of inputs provided to the machine learning model. In some embodiments, an ML system, model, or neural network described herein is an artificial neural network. In some embodiments, an ML system, model, or neural network described herein is a convolutional neural network. In some embodiments, an ML system, model, or neural network described herein is a recurrent neural network. In at least one embodiment, an ML system, model, or neural network described herein is a Bayes classifier. As used herein, a "machine learning system" may refer to one or multiple ML models that cooperatively generate one or more outputs based on corresponding inputs. For example, an ML system may refer to any system architecture having multiple discrete ML components that consider different kinds of information or inputs.

As used herein, an "instance" refers to an input object that may be provided as an input to an ML system to use in generating an output, such as a species of contaminant present, a concentration of contaminant present, or a rate of change in a contaminant present. For example, an instance may refer to any event in which the contaminant is present. For example, a first contour or other measurement received at the microcontroller may be related to a first contaminant being present in the sample portion of the immersion working fluid. In another example, a second contour or other measurement received at the microcontroller may be related to a second contaminant being present in the sample portion of the immersion working fluid. In another example, a change in a contour or other measurement received at the microcontroller may be related to an increasing concentration of a contaminant in the sample portion of the immersion working fluid.

In some embodiments, the machine learning system has a plurality of layers with an input layer configured to receive at least one input training dataset or input training instance and an output layer, with a plurality of additional or hidden layers therebetween. The training datasets can be input into the ML system to train the ML system and identify individual and combinations of contaminants or other attributes of the training instances that allow the microcontroller to identify concentrations of known or unknown contaminants.

In some embodiments, the machine learning system can receive multiple training datasets concurrently and learn from the different training datasets simultaneously.

In some embodiments, the machine learning system includes a plurality of machine learning models that operate together. Each of the machine learning models has a plurality of hidden layers between the input layer and the output layer. The hidden layers have a plurality of input nodes, where each of the nodes operates on the received inputs from the previous layer. In a specific example, a first hidden layer has a plurality of nodes and each of the nodes performs an operation on each instance from the input layer. Each node of the first hidden layer provides a new input into each node of the second hidden layer, which, in turn, performs a new operation on each of those inputs. The nodes of the second hidden layer then passes outputs, such as identified clusters, to the output layer.

In some embodiments, each of the nodes has a linear function and an activation function. The linear function may attempt to optimize or approximate a solution with a line of best fit, such as reduced power cost or reduced latency. The activation function operates as a test to check the validity of the linear function. In some embodiments, the activation function produces a binary output that determines whether the output of the linear function is passed to the next layer of the machine learning model. In this way, the machine learning system can limit and/or prevent the propagation of poor fits to the data and/or non-convergent solutions.

The machine learning model includes an input layer that receives at least one training dataset. In some embodiments, at least one machine learning model uses supervised training. In some embodiments, at least one machine learning model uses unsupervised training. Unsupervised training can be used to draw inferences and find patterns or associations from the training dataset(s) without known outputs. In some embodiments, unsupervised learning can identify clusters of similar labels or characteristics for a variety of training instances and allow the machine learning system to extrapolate the performance of instances with similar characteristics.

In some embodiments, semi-supervised learning can combine benefits from supervised learning and unsupervised learning. As described herein, the machine learning system can identify associated labels (such as known contaminants or concentrations of contaminants) or characteristic between instances, which may allow a training dataset with known outputs and a second training dataset including more general input information to be fused. Unsupervised training can allow the machine learning system to cluster the instances from the second training dataset without known outputs and associate the clusters with known outputs from the first training dataset.

In some embodiments, the immersion cooling system includes electrochemical sensors positioned at variety of locations in the immersion cooling system. For example, a first electrochemical sensor may be positioned in a lower portion of the immersion chamber with the heat-generating components. The first electrochemical sensor may be positioned to measure one or more contaminants that are present in the liquid working fluid in contact with the heat-generating components. As described herein, a two-phase immersion working fluid presents an increased risk of dendritic growth during vaporization of the liquid working fluid in contact with the heat-generating components. For at least that reason, a first electrochemical sensor positioned to measure contaminants proximate to the heat-generating components may be desirable.

In another example, a second electrochemical sensor may be positioned proximate a liquid-vapor boundary between the liquid working fluid and the vapor working fluid. The second electrochemical sensor may measure a contaminant concentration at or near the top of the liquid working fluid in the immersion chamber to provide a relative concentration between the lower portion proximate the first electrochemical sensor and the top portion, for example, to aide in determining a source or source location of the contaminants in the liquid working fluid.

In yet another example, one or more third electrochemical sensors may be positioned proximate the heat-generating components, such as within a cooling volume proximate a heat-generating component 614. The one or more third electrochemical sensors may measure the presence of the contaminants proximate the heat source in the immersion chamber and, therefore, the amount of contaminants that are present in the boiling portion of the liquid working fluid. As described herein, the liquid working fluid boiling can increase the rate of deposition of the contaminant ions and/or rate of dendritic growth on the heat-generating components, such as on pins or interconnects of a computing device. Measuring the contaminants proximate to the heat-generating components can provide the microcontroller with information to predict a risk of damage or failure to the heat-generating components.

In a further example, a fourth electrochemical sensor may be positioned in or proximate to the condenser. In some embodiments, the condenser condenses the vapor working fluid into a condensate liquid working fluid in or contacting the condenser. In at least one example, the liquid working fluid, upon boiling, converts into a vapor working fluid that does not contain the contaminant ions, and the condensate liquid working fluid in or on the condenser does not contain the contaminant ions, unless the at least some contaminant ions in the liquid working fluid originate from the condenser. Measuring the contaminant concentrations at or in the condenser with a fourth electrochemical sensor may provide the microcontroller with information related to a source or source location of the contaminant ions in the liquid working fluid.

In a yet further example, a fifth electrochemical sensor is located at a first end of the return conduit of the immersion cooling system and/or a sixth electrochemical sensor positioned at a second end of the return conduit. In some embodiments, the immersion cooling system delivers condensate liquid working fluid from the condenser to the immersion chamber through the return conduit. By detecting a contaminant and/or measuring a contaminant level at one or more locations in the return conduit, the fifth electrochemical sensor and/or sixth electrochemical sensor can provide the microcontroller with information related to a source or source location of the contaminant ions in the liquid working fluid.

In some embodiments, the microcontroller calculates a concentration of contaminants in the liquid working fluid at one or more locations in the immersion cooling system. The microcontroller or other control plane of the immersion cooling system may suggest or automatically enact remediation to the liquid working fluid to remove contaminants from the liquid working fluid and/or replace the contaminated liquid working fluid with new, uncontaminated working fluid.

In some embodiments, a method of measuring and remediating a liquid working fluid in an immersion cooling system includes positioning a sample portion of an immersion working fluid in a sampling region between a first electrode and a second electrode and applying a stimulus signal with a static voltage across the sampling region with the first electrode and second electrode. The method includes varying a frequency of the input signal and measuring an output signal across the sampling region as described herein.

In some embodiments, the method is performed inline while the immersion cooling system is operating. For example, the sample portion of the immersion working fluid of may be a portion of the liquid working fluid in an immersion chamber, in a condenser, in a return conduit, or other portion of the immersion cooling system. Sampling at multiple times and/or at multiple locations in the immersion cooling system can allow a microcontroller to determine a concentration of a contaminant based at least partially on the measured output signal.

In some embodiments, the method optionally includes remediating a portion of the immersion working fluid. For example, remediating a portion of the immersion working fluid may include changing one or more filters in the immersion cooling system, such as proximate an inlet or outlet of the condenser, proximate an inlet or outlet of the immersion tank or chamber, proximate an inlet or outlet of a return conduit, or at other locations in the immersion cooling system.

In another example, remediating a portion of the immersion working fluid may include adding uncontaminated immersion working fluid to the immersion cooling system, such as opening a valve to add uncontaminated immersion working fluid to the immersion cooling system. Adding uncontaminated immersion working fluid to the immersion cooling system may dilute the contaminant ions in the existing immersion working fluid, reducing effects of the contaminant ions on one or more properties of the immersion working fluid, such as conductivity, boiling temperature, or other properties. In other example, diluting the contaminant ions in the immersion working fluid may reduce a deposition rate and reduce dendritic growth. In at least one embodiment, adding uncontaminated immersion working fluid to the immersion cooling system includes opening a valve to allow the uncontaminated immersion working fluid to flow from a reservoir through the valve into the immersion cooling system. For example, the valve may be controlled by the microcontroller, and the microcontroller may open the valve at least partially based on the measured output signal(s).

In yet another example, remediating a portion of the immersion working fluid may include replacing contaminated immersion working fluid with an uncontaminated immersion working fluid. Replacing contaminated immersion working fluid with an uncontaminated immersion working fluid may include opening at least a first valve to drain a portion of the contaminated immersion working fluid from the immersion cooling system and opening at least a second valve to allow uncontaminated immersion working fluid to flow from a reservoir through the valve into the immersion cooling system. In at least one embodiment, the valves may be controlled by the microcontroller, and the microcontroller may open the valves at least partially based on the measured output signal(s).

In an example, the immersion cooling system may include a reservoir containing an uncontaminated immersion working fluid and a collection tank configured to capture at least a portion of the contaminated liquid working fluid. In some embodiments, the reservoir is connected to the return conduit or other inlet to the immersion chamber to introduce the uncontaminated immersion working fluid into the immersion chamber. In other examples, the reservoir may be connected to the immersion chamber directly or by a dedicated conduit, or the reservoir may be connected to the condenser to deliver the uncontaminated immersion working fluid into the immersion cooling system via the condenser.

In some embodiments, a first valve controls a flow of the uncontaminated immersion working fluid into the immersion cooling system. The first valve may be controlled by the microcontroller. In other embodiments, the first valve may be controlled by another control plane that receives contaminant and/or contaminant concentration information from the microcontroller.

A collection tank may be connected to the immersion cooling system by a second valve. In some embodiments, the collection tank is connected to the return conduit or other conduit of the immersion chamber to receive contaminated liquid working fluid 808 from the immersion chamber. In other examples, the collection tank may be connected to the immersion chamber directly or by a dedicated conduit, or the collection tank may be connected to the condenser to receive the contaminated liquid working fluid from the immersion cooling system via the condenser.

In some embodiments, the second valve controls a flow of the contaminated liquid working fluid into the immersion cooling system. The second valve may be controlled by the microcontroller. In other embodiments, the second valve may be controlled by another control plane that receives contaminant and/or contaminant concentration information from the microcontroller. In at least one embodiment, the microcontroller or other control plane opens the first valve and the second valve at least partially simultaneously (e.g., a period of time when the first valve is open at least partially overlaps a period of time when the second valve 866 is open) to introduce uncontaminated immersion working fluid into the immersion cooling system from the reservoir while at least a portion of the contaminated liquid working fluid is removed into the collection tank.

The present disclosure relates to systems and methods for cooling heat-generating components of a computer or computing device according to at least the examples provided in the sections below:

[A1] In some embodiments, an immersion cooling system includes an immersion tank defining an immersion chamber therein, an immersion working fluid, a first electrode, and a second electrode. The immersion working fluid is positioned at least partially in the immersion chamber. The first electrode is electrically coupled to an electrical power source, and the second electrode is positioned proximate to the first electrode and defines a sampling region therebetween. A sample portion of the immersion working fluid is positioned in the sampling region, and the second electrode is coupled to a microcontroller configured to measure at least a current across the sampling region between the first electrode and the second electrode.

[A2] In some embodiments, the electrical power source of [A1] includes a direct current (DC) source and an alternating current (AC) stimulus.

[A3] In some embodiments, the electrical power source of [A1] or [A2] provides a stimulus signal to the first electrode and the stimulus signal includes a static voltage.

[A4] In some embodiments, the stimulus signal of [A3] further comprises a swept sine wave.

[A5] In some embodiments, the microcontroller of [A4] records a plurality of impedance data points

[A6] In some embodiments, the first electrode and the second electrode of any of [A1] through [A5] are located in the immersion chamber.

[A7] In some embodiments, the first electrode and the second electrode of any of [A1] through [A5] are located in a condenser.

[A8] In some embodiments, the first electrode and the second electrode of any of [A1] through [A5] are located in a return conduit connected to the immersion chamber.

[A9] In some embodiments, the first electrode and the second electrode of any of [A1] through [A5] are located in a cooling volume proximate a heat-generating component.

[A10] In some embodiments, the first electrode and the second electrode of any of [A1] through [A9] form a first electrochemical sensor, and the system further includes a second electrochemical sensor positioned in the immersion chamber and in communication with the microcontroller.

[B1] In some embodiments, a method of measuring a liquid working fluid in an immersion cooling system includes circulating an immersion working fluid in the immersion cooling system, positioning a sample portion of an immersion working fluid in a sampling region between a first electrode and a second electrode, applying a stimulus signal with a static voltage across the sampling region with the first electrode and second electrode, varying a frequency of the stimulus signal, measuring an output signal across the sampling region, and determining a first concentration of a contaminant based at least partially on the output signal.

[B2] In some embodiments, determining the concentration of the contaminant of [B1] includes inputting the measured output signal into a machine learning (ML) model.

[B3] In some embodiments, varying a frequency of the input signal of [B1] or [B2] includes changing a DC signal with an AC stimulus.

[B4] In some embodiments, positioning a sample portion of an immersion working fluid in a sampling region between a first electrode and a second electrode of any of [B1] through [B3] includes flowing the sample portion of the immersion working fluid through a return conduit.

[B5] In some embodiments, circulating the immersion working fluid in the immersion cooling system of any of [B1] through [B4] includes vaporizing at least a portion of the immersion working fluid.

[B6] In some embodiments, the first electrode and a second electrode of any of [B1] through [B5] are a first electrochemical sensor at a first location in the immersion cooling system, and the method further includes measuring a second output signal with a second electrochemical sensor at a second location in the immersion cooling system.

[B7] In some embodiments, the method of [B6] further includes determining a second concentration of the contaminant based at least partially on the second output signal.

[C1] In some embodiments, a method of measuring and remediating a liquid working fluid in an immersion cooling system includes circulating an immersion working fluid in the immersion cooling system, positioning a sample portion of an immersion working fluid in a sampling region between a first electrode and a second electrode, applying a stimulus signal with a static voltage across the sampling region with the first electrode and second electrode, varying a frequency of the stimulus signal, measuring an output signal across the sampling region, determining a concentration of a contaminant based at least partially on the output signal with a microcontroller in communication with the first electrode and second electrode, and remediating the immersion working fluid based at least partially on the concentration of the contaminant using the microcontroller.

[C2] In some embodiments, remediating the immersion working fluid of [C1] includes opening a valve to add uncontaminated immersion working fluid to the immersion cooling system.

[C3] In some embodiments, remediating the immersion working fluid of [C1] or [C2] includes opening a valve to remove at least a portion of the immersion working fluid from the immersion cooling system.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about", "substantially", or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

It should be understood that any directions or reference frames in the preceding description are merely relative directions or movements. For example, any references to "front" and "back" or "top" and "bottom" or "left" and "right" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. An immersion cooling system comprising:
an immersion tank defining an immersion chamber in the immersion tank;
an immersion working fluid positioned at least partially in the immersion chamber;
a first electrode configured to electrically couple to an electrical power source including a direct current (DC) source and an alternating current (AC) stimulus;
a second electrode positioned proximate to the first electrode and defining, between the first electrode and the second electrode, a sampling region for positioning a sample portion of the immersion working fluid;
an ammeter in electrical communication with the second electrode and configured to measure current across the sampling region between the first electrode and the second electrode; and
a microcontroller coupled to the second electrode wherein the microcontroller is configured to apply to the sample portion in the sampling region via the second electrode one or more stimulus signals powered in operation by the electrical power source and receive the current measured by the ammeter.

2. The immersion cooling system of claim 1, further comprising a voltmeter configured to measure voltage across the sampling region between the first electrode and the second electrode and wherein the microcontroller is further configured to sweep one or more stimulus signals from the direct current (DC) source and the alternating current (AC) stimulus through a range of voltages and receive the measured voltage and, based on the measured voltage and the measured current, record a plurality of impedance data points from the one or more stimulus signal sweeps.

3. The immersion cooling system of claim 1, wherein and the stimulus signal includes a static voltage.

4. The immersion cooling system of claim 3, wherein the stimulus signal further comprises a swept sine wave superimposed on the static voltage.

5. The immersion cooling system of claim 4, further comprising a voltmeter configured to measure voltage across the first electrode and the second electrode and wherein the microcontroller is further configured to sweep one or more stimulus signals from the direct current (DC) source and the alternating current (AC) stimulus through a range of voltages and receive the measured voltage and, based on the measured voltage and the measured current, record a plurality of impedance data points from one or more stimulus signal sweeps.

6. The immersion cooling system of claim 1, wherein the first electrode and the second electrode are located within the immersion chamber.

7. The immersion cooling system of claim 1, further comprising a condenser wherein the first electrode and the second electrode are located within the condenser.

8. The immersion cooling system of claim 1, further comprising a return conduit connected to the immersion chamber wherein the first electrode and the second electrode are located within the return conduit.

9. The immersion cooling system of claim 1, further comprising a heat generating component proximate to a cooling volume wherein the first electrode and the second electrode are located in the cooling volume proximate the heat-generating component.

10. The immersion cooling system of claim 1, wherein the first electrode and the second electrode constitute a first electrochemical sensor; and wherein the immersion cooling system further comprises a second electrochemical sensor positioned within the immersion chamber and in communication with the microcontroller.

11. A method of determining contaminant concentration in an immersion working fluid using the immersion cooling system of claim 1, the method comprising:

circulating the immersion working fluid in the immersion cooling system;

positioning the sample portion of the immersion working fluid in the sampling region between the first electrode and the second electrode;

applying a stimulus signal with a static voltage across the sampling region with the first electrode and second electrode;

varying a frequency of the stimulus signal;

measuring a first output signal across the sampling region; and determining a first concentration of a contaminant based at least partially on the measured first output signal.

12. The method of claim 11, wherein the determining the first concentration of the contaminant includes inputting the measured first output signal into a machine learning (ML) model.

13. The method of claim 11, wherein the varying the frequency of the input signal includes changing a DC signal by superimposing the DC signal with an AC stimulus.

14. The method of claim 11, wherein the positioning the sample portion of the immersion working fluid in the sampling region between the first electrode and the second electrode includes flowing the sample portion of the immersion working fluid through a return conduit.

15. The method of claim 11, wherein the circulating the immersion working fluid in the immersion cooling system includes vaporizing at least a portion of the immersion working fluid.

16. The method of claim 11, wherein the first electrode and the second electrode constitute a first electrochemical sensor at a first location in the immersion cooling system, the method further comprising:

measuring a second output signal with a second electrochemical sensor at a second location in the immersion cooling system.

17. The method of claim 16, further comprising determining a second concentration of the contaminant at a second time based at least partially on the measured second output signal.

18. The method of claim 11, wherein the determining the first concentration of the contaminant based at least partially on the measured first output signal comprises using the microcontroller in communication with the first electrode and second electrode, the method further comprising remediating the immersion working fluid based at least partially on the first concentration of the contaminant using the microcontroller.

19. The method of claim 18, wherein the remediating the immersion working fluid based at least partially on the first concentration of the contaminant using the microcontroller includes adding uncontaminated immersion working fluid to the immersion cooling system by opening a valve.

20. The method of claim 18, wherein the remediating the immersion working fluid based at least partially on the first concentration of the contaminant using the microcontroller includes removing at least a portion of the immersion working fluid from the immersion cooling system by opening a valve.

* * * * *